United States Patent [19]

Mohacsi et al.

[11] Patent Number: 4,992,432
[45] Date of Patent: Feb. 12, 1991

[54] 3-PHENYL-THIAZEPINONES AS CALCIUM REGULATING AGENTS

[75] Inventors: Erno Mohacsi, Summit; Jay P. O'Brien, Cedar Grove, both of N.J.

[73] Assignee: Hoffmann-La Roche Inc., Nutley, N.J.

[21] Appl. No.: 478,378

[22] Filed: Feb. 12, 1990

[51] Int. Cl.$^5$ .................... A61K 31/55; C07D 281/06
[52] U.S. Cl. .................................... 514/211; 540/488
[58] Field of Search ........................ 540/488; 314/211

[56] References Cited

U.S. PATENT DOCUMENTS 4,808,580 2/1989 Mohacsi et al. ................ 514/211

*Primary Examiner*—Robert T. Bond
*Attorney, Agent, or Firm*—George M. Gould; Bernard S. Leon; Ellen Ciambrone Coletti

[57] ABSTRACT

Compounds of the formula

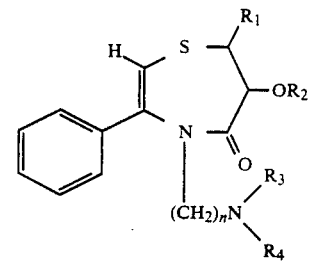

wherein $R_1$ is phenyl substituted with 1 to 3 substituents selected from the group consisting of halogen and lower alkoxy; $R_2$ is hydrogen, lower alkyl, lower alkanoyl, lower cycloalkanoyl,

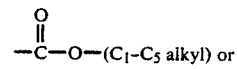

or

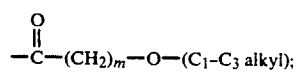

$R_3$ and $R_4$ are independently lower alkyl, phenyl lower alkyl or together form a piperidine or pyrrolidine ring; n is 2 ro 4; m is 1 to 2; and pharmaceutically acceptable acid addition salts thereof, with the proviso that when $R_1$ is 4-methoxyphenyl, $R_2$ is hydrogen and $R_3$ and $R_4$ are methyl; and n is 2, the compound of formula I cannot be in the (−)-cis form, are described. The compounds of formula I are active as calcium channel blockers and accordingly, are useful as agents for treating ischemia.

27 Claims, No Drawings

3-PHENYL-THIAZEPINONES AS CALCIUM REGULATING AGENTS

BRIEF SUMMARY OF THE INVENTION

The invention relates to compounds of the formula

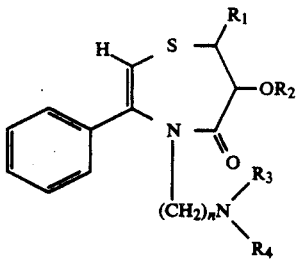

wherein $R_1$ is phenyl substituted with 1 to 3 substituents selected from the group consisting of halogen and lower alkoxy; $R_2$ is hydrogen, lower alkyl, lower alkanoyl, lower cycloalkanoyl,

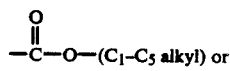

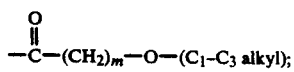

$R_3$ and $R_4$ are independently lower alkyl phenyl lower alkyl or together form a piperidine or pyrrolidine ring; n is 2 to 4; m is 1 to 2; and pharmaceutically acceptable acid addition salts thereof. The compounds of formula I are active as calcium channel blockers and accordingly, are useful as agents for treating ischemia.

DETAILED DESCRIPTION OF THE INVENTION

As used herein, the term "lower alkyl" denotes a straight or branched-chain alkyl group containing 1 to 4 carbon atoms, for example, methyl, ethyl, propyl, isopropyl, butyl, and the like. Alternatively, the number of carbon atoms in an alkyl group is designated herein as in "$C_1$-$C_3$ alkyl" which denotes a straight or branched chain alkyl group containing 1 to 3 carbon atoms. The term "lower alkoxy" denotes a straight or branched chain lower alkoxy group containing 1 to 4 carbon atoms, for example, methoxy, ethoxy, propoxy, isopropoxy, butoxy, and the like. The term "halogen" denotes the halogens, that is, bromine, chlorine, fluorine and iodine. The term "lower alkanoyl" denotes a straight or branched chain alkanoyl group of 2 to 5 carbon atoms, for example, acetyl, propionyl, butyryl, isopropionyl and the like. The term "lower cycloalkanoyl" denotes a lower cycloalkanoyl group containing 3 to 6 carbon atoms, for example, cyclopropanoyl, cyclobutanoyl, cyclopentanoyl, and cyclohexanoyl. The term "phenyl lower alkyl" denotes a lower alkyl substituted by a phenyl, for example, phenylmethyl, phenylethyl, phenylpropyl, phenylbutyl and the like.

As used in the formulas herein a solid line— indicates a substituent that is above the plane of the sulfur and nitrogen containing ring, a dotted line ⦀⦀ indicates a substituent that is below the plane of the sulfur and nitrogen containing ring.

The invention relates to compounds of the formula

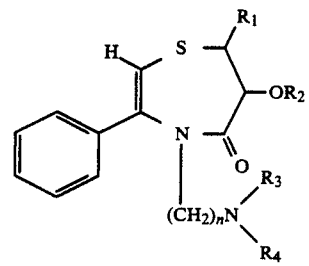

wherein $R_1$ is phenyl substituted with 1 to 3 substituents selected from the group consisting of halogen and lower alkoxy; $R_2$ is hydrogen, lower alkyl, lower alkanoyl, lower cycloalkanoyl,

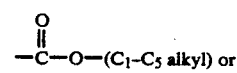

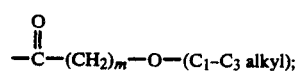

$R_3$ and $R_4$ are independently lower alkyl, phenyl lower alkyl or together form a piperidine or pyrrolidine ring; n is 2 to 4; m is 1 to 2; and pharmaceutically acceptable acid addition salts thereof are described. The compounds of formula I are active as calcium channel blockers and accordingly, are useful as agents for treating ischemia.

The compounds of formula I contain 2 asymmetric centers at the 6- and 7-positions. Accordingly, the compounds of formula I can be stereoisomers, that is cis or trans isomers.

As used herein, the term "cis" denotes a compound wherein the $R_1$ and -$OR_2$ substituents are both on the same side of the plane of the sulfur and nitrogen containing ring. As used herein the term "(+)-cis" denotes an enantiomer having a relative configuration analogous to that of (+)-cis-6-(acetyloxy)-6,7-dihydro-7-(4-methoxyphenyl)-4-[2-(dimethylamino)ethyl]-3-phenyl-1,4-thiazepin-5(4H)-one which is a (+)-cis compound of the invention.

A compound of the formula

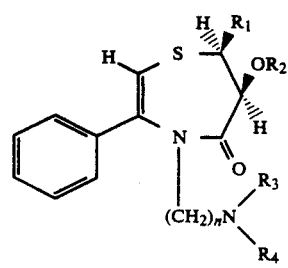

wherein $R_1$, $R_2$, $R_3$, $R_4$ and n are as described above is a (+)-cis compound of the invention.

A compound of the formula

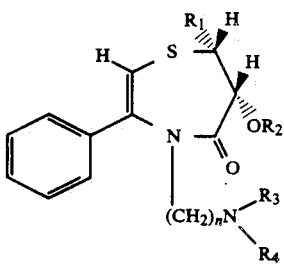

wherein $R_1$, $R_2$, $R_3$, $R_4$ and n are as described above is an enantiomer of a compound of formula I' and a (−)-cis compound of the invention.

Preferred compounds of the invention are cis compounds.

Especially preferred compounds of the invention are (+)-cis compounds.

As used herein the term "trans" denotes a compound of formula I wherein the $R_1$ and $OR_2$ substituents are on opposite sides of the plane of the sulfur and nitrogen containing ring.

A compound of the formula

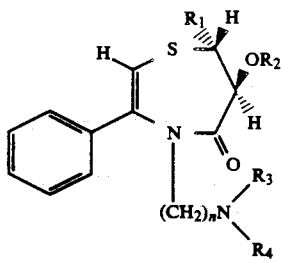

wherein $R_1$, $R_2$, $R_3$, $R_4$, and n are as described above is a trans compound of the invention.

A compound of the formula

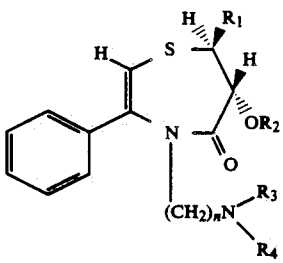

wherein $R_1$, $R_2$, $R_3$, $R_4$, and n are as described above is the enantiomer of a compound of formula I''', and another trans compound of the invention.

As used herein the term an "erythro compound" refers to a compound having the following Fischer projection as a formula:

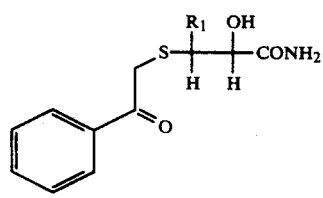

As used herein, the term a "threo compound" refers to a compound having the following Fischer projection as a formula.

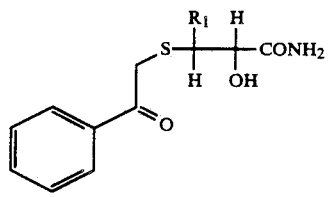

An erythro compound corresponds to a compound of formula IV. A threo compound refers to a compound of formula V.

According to the invention, an erythro compound is converted to a rac.-cis compound of formula I, while a threo compound is converted to a rac.-trans compound of formula I.

Preferred compounds of formula I are those wherein $R_1$ is 4-lower alkoxyphenyl and $R_2$ is hydrogen or lower alkanoyl, $R_3$ and $R_4$ are independently lower alkyl, and n is 2 to 3. Of these, as has been pointed out above, cis compounds are preferred and (+)-cis compounds are especially preferred.

More preferred compounds of formula I are those wherein $R_1$ is 4-ethoxyphenyl, or more preferably 4-methoxyphenyl; $R_2$ is propionyl or more preferably hydrogen or acetyl; n is 2; and $R_3$ and $R_4$ are each ethyl or more preferably are each methyl. Of these, as has been pointed above, cis compounds are preferred and (+)-cis compounds are especially preferred. Exemplary of compounds of formula I are:

trans-rac.-6-(Acetyloxy)-6,7-dihydro-7-(4-methoxyphenyl)-4-[2-dimethylamino) ethyl]-3-phenyl-1,4-thiazepin-5(4H)-one; trans-rac.-6,7-Dihydro-6-hydroxy-7-(4-methoxyphenyl)-4-[2-(dimethylamino) ethyl]-3-phenyl-1,4-thiazepin-5(4H)-one;

(−)-cis-6-(Acetyloxy)-6,7-dihydro-7-(4-methoxyphenyl)-4-[2-dimethylamino) ethyl]-3-phenyl-1,4-thiazepin-5(4H)-one;

(−)-cis-6,7-Dihydro-6-hydroxy-7-(4-methoxyphenyl)-4-[2-(dimethylamino) ethyl]-3-phenyl-1,4-thiazepin-5(4H)-one; and (+)-cis-6,7-Dihydro-6-hydroxy-7-(4-methoxyphenyl)-4-[2-(dimethylamino) ethyl]-3-phenyl-1,4-thiazepin-5(4H)-one A most preferred compound of the invention is:

(+)-cis-6-(Acetyloxy)-6,7-dihydro-7-(4-methoxyphenyl)-4-[2(dimethylamino) ethyl]-3-phenyl-1,4-thiazepin-5(4H)-one.

The invention also relates to intermediates of the formula:

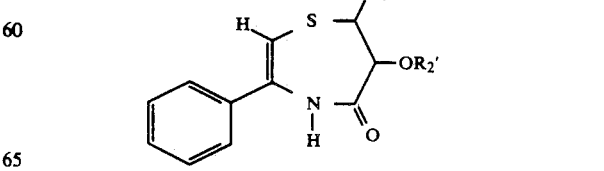

wherein $R_1$ is as described above, and $R_2'$ is lower alkyl, lower alkanoyl, lower cycloalkanoyl,

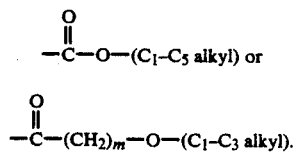

Exemplary of compounds of formula X are:
cis-rac.-6-(Acetyloxy)-6,7-dihydro-7-(4-methoxyphenyl)-3-phenyl-1,4-thiazepin-5(4H)-one; and trans-rac.-6-(Acetyloxy)-6,7-dihydro-7-(4-methoxyphenyl)-3-phenyl-1,4-thiazepin-5(4H)-one.

The invention also relates to calcium channel blocking compositions comprising an effective amount of a compound of formula I and a pharmaceutically inert carrier material.

The invention also relates to a method of inducing calcium channel blockage, which comprises administering to a warm-blooded animal in need of such treatment an effective amount of a compound of formula I.

The invention also relates to a process for preparing compounds of formula I.

The compounds of formula I can be prepared as shown in Formula Scheme I below.

As used in Formula Scheme I below

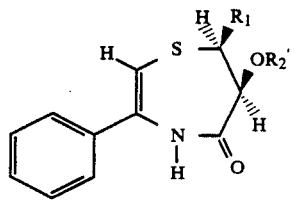

(±)-cis refers to the (±)-cis compound, that is, the enantiomeric mixture of this cis compound.

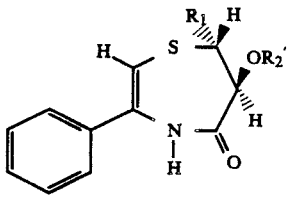

(±)-trans refers to the (±)-trans compound, that is the enantiomeric mixture of this trans compound. Similar structural formulas have similar meanings throughout these schemes, and throughout this specification. However, solid lines and dotted lines are not used in the structure of the (±)-cis-base of formula Ia* of Formula Scheme 2. The drawing used makes clear that the starting compound of formula Ia* is the (±)-cis-base while the final products are the (+)-cis-base and the (−)-cis-base, respectively.

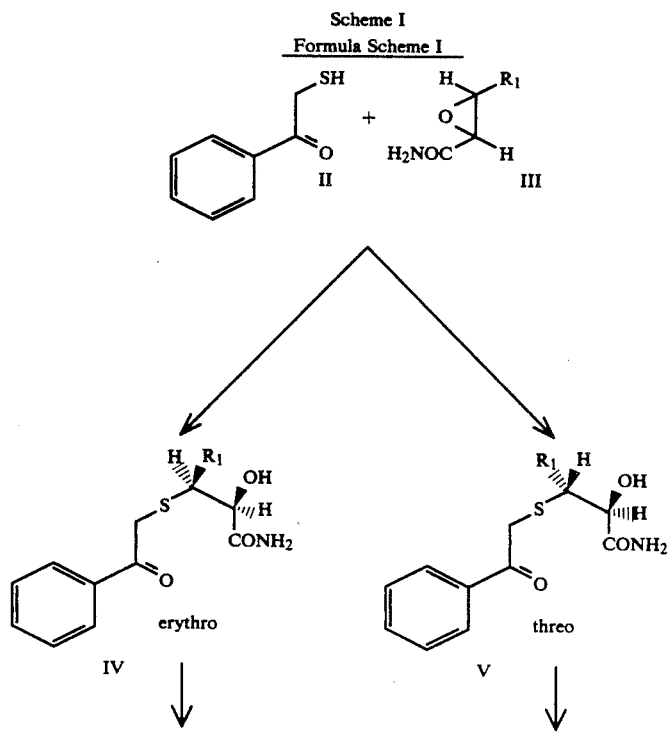

Scheme I
Formula Scheme I

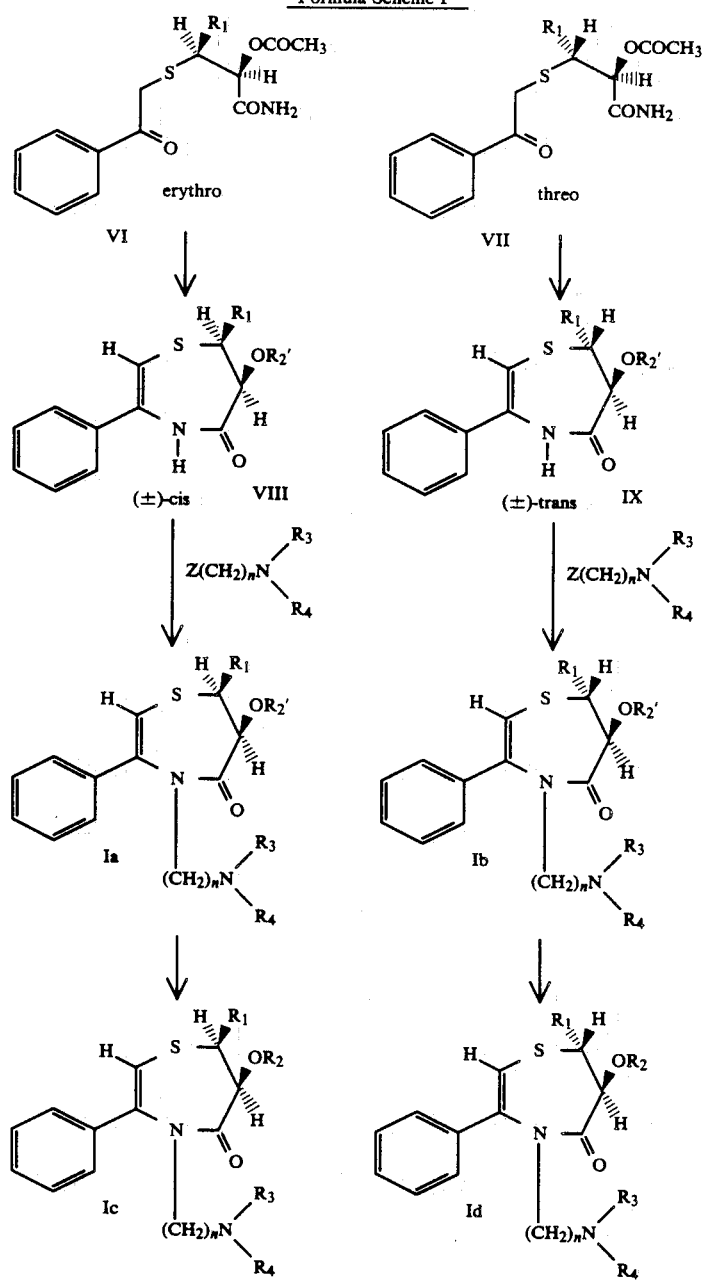

wherein $R_1$, $R_2'$, $R_3$, $R_4$, and n are as described above.

In connection with Formula Scheme I, the compound of formula

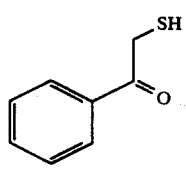

which is known is reacted with a compound of the formula

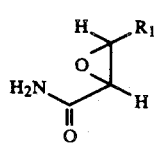

wherein $R_1$ is as described above which are known or can be prepared in accordance with the examples below. In the reaction, a compound of formula III is added to a solution, under argon or nitrogen, of a compound of formula II in a nonpolar aromatic solvent such as ethylbenzene, benzene, or more preferably toluene. The solution is brought to reflux, for a period of 1 to 10 hours, more preferably about 2-3 hours. There is isolated upon conventional chromatographic work-up a compound of the formula:

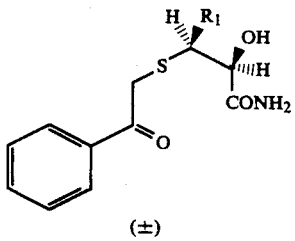

(±)

and there is also isolated a compound of the formula V.

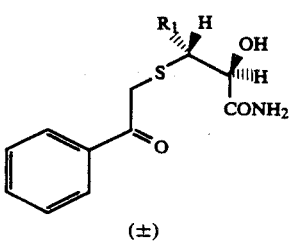

(±)

wherein $R_1$ is as described above.

Alternatively, a compound of formula V may be prepared directly by the reaction of the compound of formula II with a compound of formula III in a polar organic solvent such as ethanol, or more preferably acetonitrile in the presence of a base such as potassium carbonate at reflux under inert atmosphere such as argon or nitrogen. Upon conventional work-up there is obtained a compound of formula V.

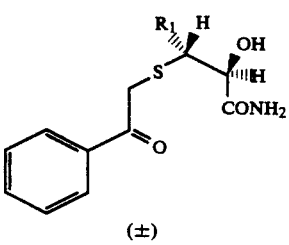

(±)

A compound of formula

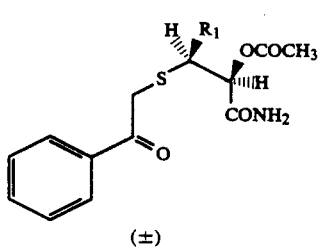

(±)

wherein $R_1$, is as described above, can be obtained by reaction with a corresponding compound of formula IV with an acylating agent such as acetic anhydride or, more preferably, acetyl chloride in an inert organic solvent such as methylene chloride, in the presence of a base such as pyridine. The reaction is carried out at 0° C. to about room temperature for about 1 to about 20 hours. Upon conventional work-up a compound of formula VI is obtained.

Similarly, a compound of formula

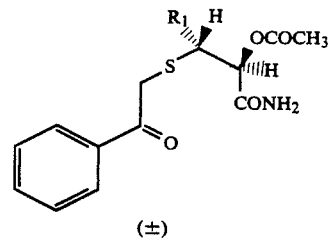

(±)

wherein $R_1$, is as described above, may be obtained by an analogous acylation of the corresponding compound of formula V.

A compound of formula VI can be cyclized in the presence of an organic acid such as p-toluenesulfonic acid in an aromatic organic solvent such as ethylbenzene, benzene, or more preferably toluene, so as to obtain a compound of the formula

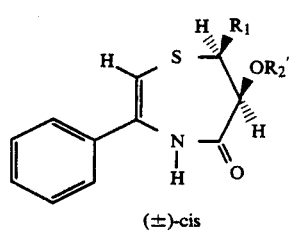

(±)-cis wherein $R_1$ and $R_2$' are as described above.

Similarly, a compound of formula

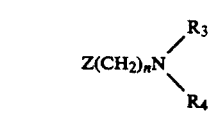

(±)-trans wherein $R_1$, is as described above, may be obtained by an analogous cyclization of the corresponding compound of formula VII.

Compounds of formula VIII and IX may be converted to the corresponding compounds of formula Ia and Ib by reaction with a compound of the formula:

$$Z(CH_2)_nN\begin{array}{c}R_3\\ \\R_4\end{array} \quad X$$

wherein $R_3$, $R_4$ and n are as described above, and Z is halogen, preferably chlorine.

The reaction is carried out by reacting an alkali metal salt of a compound of formula VIII or IX, such as the sodium or more preferably potassium salt thereof with an aminoalkyl halide of formula X, preferably the chloride thereof, in a polar organic solvent such as acetone, methyl acetate, or more preferably ethyl acetate, at about 40° to about 80°, or at the reflux temperature of the solvent employed, which in the case of ethyl acetate is 77°, for a period of about 1 hour to about 17 hours. The reaction is carried out in the presence of a base, such as, potassium hydroxide in acetone or more preferably potassium carbonate in acetone or in a lower alkyl acetate. Separation of a corresponding compound of formula Ia or Ib can be by conventional means such as, crystallization.

A compound of formula Ia or Ib may be hydrolyzed to the corresponding compound of formula Ic or Id by reaction with an acid such as HCl at room temperature in ethanol, or a base such as sodium hydroxide in ethanol, or more preferably, potassium carbonate, in a polar organic solvent such as methanol, propanol, or ethanol or more preferably ethyl acetate at an elevated temperature, for ½ hour to 4 hours. Upon conventional work up the corresponding compound of formula Ic or Id is obtained.

A compound of formula Ic or Id, which is encompassed by compounds of formula I, can be acylated by reaction with a lower alkanoic anhydride, such as propionic anhydride, acetic anhydride, or a lower alkanoyl halide for example, acetyl, propionyl or butyryl chloride optionally in the presence of a base such as, pyridine, triethylamine, or dimethylaniline at room temperature or up to about 115°.

Alternatively, compounds of formula I wherein $R_2$ is lower alkyl can be obtained by reacting an alkali metal salt of a compound of formula Ic or Id such as a sodium salt (prepared by reacting a compound of formula Ic or Id with an alkali metal hydride like sodium hydride), with an alkylating agent such as dialkyl sulfate, more particularly dimethyl sulfate in an aromatic solvent such as toluene or more preferably benzene, at about reflux temperature for a period of about 10 minutes to about 2 hours. The resulting compound of formula I can be isolated by conventional means such as crystallization.

Alternatively, a compound of formula I wherein $R_2$ is

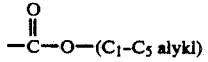

can be obtained by a reaction of a compound of formula Ic or Id with an alkyl halo formate such as ethyl chloroformate in a basic solvent such as pyridine at about ice bath temperatures. The resulting compound of formula I can be isolated by conventional means such as crystallization.

A compound of formula I wherein $R_2$ is

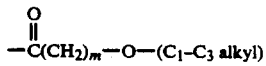

can be prepared by reacting a compound of formula Ic or Id with an alkoxy alkanoyl halide such as, methoxyacetyl chloride in a basic solvent such as pyridine at about ice bath temperatures. The resulting compound of formula I can be isolated by conventional means such as crystallization.

A compound of formula I wherein $R_2$ is cycloalkyl carbonyl can be obtained by reacting a compound of formula Ic or Id with a cycloalkylcarboxylic acid halide such as, cyclopropane carboxylic acid chloride in a basic solvent such as pyridine at about ice bath temperatures for about 1 to about 17 hours. The resulting compound of formula I can be isolated by conventional means such as extraction.

A compound of formula I wherein $R_2$ is other than hydrogen can be converted into a corresponding acid addition salt by treatment with an organic acid such as, acetic acid, oxalic acid, malonic acid, tartaric acid, maleic acid, citric acid, lactic acid, malic acid, or fumaric acid and a suitable organic solvent such as, ethyl acetate, acetone, methanol, or ethanol. Alternatively, a compound of formula I wherein $R_2$ is other than hydrogen can be converted into a corresponding acid addition salt by treatment with an inorganic acid such as sulfuric acid, hydrobromic acid, or more preferably hydrochloric acid, except in those instances where the $R_2$ substituent would be cleaved by such treatment. The resulting compound of formula I wherein $R_2$ is hydrogen can be converted into the corresponding acid addition salt by treatment with an organic acid as described above or an inorganic acid such as, hydrochloric acid, in a suitable organic solvent such as ethyl acetate.

A compound of formula I may be resolved into its optically active enantiomers. The resolution of a particular cis compound of formula Ia*, that is, cis-rac.-6-(acetyloxy)-6,7-dihydro-7-(4-methoxyphenyl)-4-[2-dimethylamino) ethyl]-3-phenyl-1,4-thiazepin-5(4H)-one, is shown in Formula Scheme 2. This resolution uses d-tartaric acid and then l-tartaric acid. The resolution of other compounds of formula I may require, for example, other conventional resolving agents.

FORMULA SCHEME 2

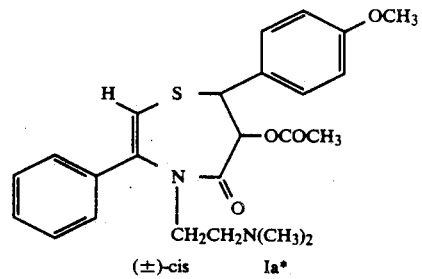

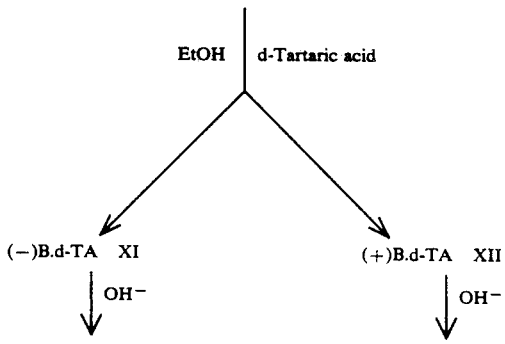

-continued
FORMULA SCHEME 2

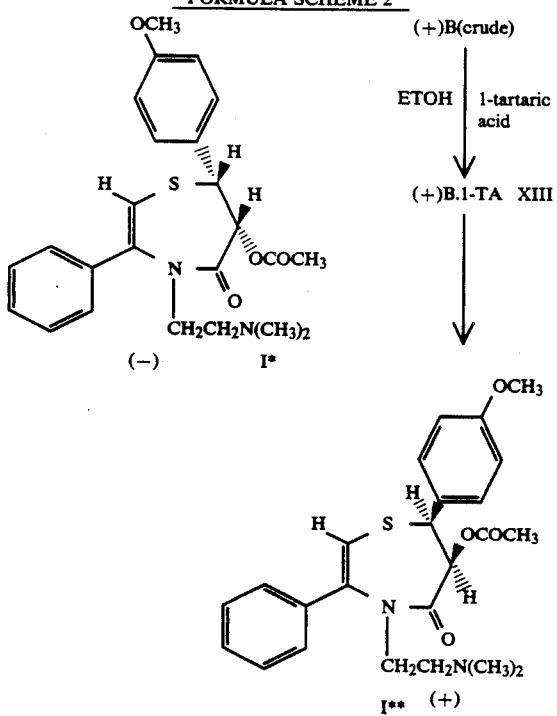

wherein (+)- and (−)B are respectively the (+)- and (−)-enantiomers of the just above-mentioned compound of formula Ia*.

In connection with Formula Scheme 2 above, the racemate of formula Ia* in a polar protic organic solvent such as ethanol is treated with a hot solution d-tartaric acid: A few seed crystals of formula XI may be added and the solution is allowed to crystallize at about room temperature, for about 1 to about 30 hours.

The crystals are a salt of formula XI of the resolving agent and the (−)-enantiomer of the compound of formula Ia* of Formula Scheme 2. The soluble salt is that of the (+)-enantiomer of the compound of formula Ia* and the resolving agent. This is the solution of formula XII in Formula Scheme 2 above.

The crystals of the salt of formula XI are collected by filtration.

The crystals of the salt of formula XI can be treated in water with a base such as sodium hydroxide or more preferably concentrated ammonium hydroxide and then the aqueous suspension extracted with an organic solvent such as ethyl acetate, or more preferably methylene chloride and concentrated to obtain the (−)-enantiomer [(−)-cis--Base]of the compound of formula Ia*. This free base may be treated with an inorganic acid such as hydrogen chloride in a polar organic solvent such as ethyl acetate to form the corresponding acid addition salt thereof. This (31 )-enantiomer is the compound of formula I* in Formula Scheme 2 This (−)-enantiomer can be used in the above-described reactions of compounds of formula I.

The above solution of the salt of formula XII can be treated in water with a base such as sodium or more preferably concentrated ammonium hydroxide, and then the aqueous suspension extracted with an organic solvent such as ethyl acetate, or more preferably, methylene chloride, worked up, and concentrated to achieve the crude (+)-enantiomer of formula Ia*.

The crude (+)-enantiomer of formula Ia* may be dissolved in a hot solution of 1-tartaric acid and ethanol and allowed to crystallize at room temperature for 1 to 2 days. The salt thus formed is shown as formula XIII in Formula Scheme 2 above.

This just above-mentioned salt may be dissolved in water and treated with a base such as sodium hydroxide or more preferably concentrated ammonium hydroxide and the resulting aqueous suspension can be extracted with an organic solvent such as ethyl acetate or more preferably methylene chloride. The combined extracts can be worked up in a conventional manner to obtain the (+)-enantiomer [(+)-cis-Base]of the compound of formula Ia* of Formula Scheme 2. This (+)-enantiomer is the compound of formula I** in Formula Scheme 2. The (+)-enantiomer of the compound of formula Ia* can be used in the above-described reactions of compounds of formula Ia.

Other cis racemates of formula Ia can be similarly resolved by using other conventional resolving agents.

The compound of formula II is known and can be prepared by known methods such as those set forth in M. Yamada, K. Sotoya, T. Sabakibara, T. Takamot and R. Sudoh, J. Org. Chem., 42, 2180 (1977).

A compound of formula III is prepared from known starting materials in a manner shown in the examples below.

The compounds of formula X are known compounds or can be prepared according to known methods. Exemplary of the compounds of formula X are:
2-dimethylaminoethyl chloride;
2-dimethylaminoethyl bromide;
2-diethylaminoethyl chloride;
2-dipropylaminoethyl chloride; and
3-dimethylaminopropyl chloride.

As can be seen, formula I encompasses, formulas Ia, Ib, Ic, Id, I*, and I**.

The compounds of formula I, including the pharmaceutically acceptable acid addition salts thereof are calcium antagonists, more specifically, calcium channel blockers, and therefore useful as agents in lowering blood pressure and in treating ischemia. Their pharmacologically useful activities are demonstrated in warm-blooded animals using standard procedures which are set forth below.

The calcium channel blocking activity of compounds of formula I was determined by measuring the effect of compounds of formula I on isolated rat aortic strips.

Contraction of Rat Aortic Strips

Aortas were excised from rats, placed in Krebs-Henseleit solution, modified so as to be calcium free, with a depolarized level of potassium (45 mM), and 0.02 mM EDTA. The aorta was then helically cut into a strip. This strip was then divided into four equal segments which were hung in isolated tissue chambers, attached to the appropriate tranducers and subjected to 500 mg basal tension. After a period of stabilization under these conditions, calcium was introduced into the bath and the tissues contracted in a concentration dependent manner.

When no calcium is available in the bathing media, and the potential dependent calcium channels are opened by the high potassium level, contractility is dependent on the level of calcium introduced into the bath. By adding increments of calcium into the bath, a reproducible concentration-dependent contracture can be obtained. Treatment with a calcium channel blocker, such as diltiazem, or a compound of the invention results in an inhibition of this contractile response.

Each number in the table below was derived by first adding calcium alone to tissue and measuring contracture, and then adding calcium to tissue that had been exposed to $3 \times 10^{-7}$M of the compound to be tested and measuring contracture. The number for untreated controls was derived by measuring contracture for two runs where calcium alone was added. As can be seen, contructure was 0.7% greater for the second run of untreated controls.

Diltiazem, after a 15 minute exposure at $3 \times 10^{-7}$M, caused a marked reduction in responsiveness to 2 mM Ca++ when tested in this manner.

A compound tested was placed in the bath at $3 \times 10^{-7}$M for 15 minutes prior to, and during the acquisition of the concentration-dependent curve to calcium for that particular compound. The inhibition in contractile response at 2mMCa++ was measured as a per cent inhibition as compared to the control. The effects on the 2mM Ca++ contracture are as follows:

| Compound | % Inhibition | Number of Tests (n) |
|---|---|---|
| Diltiazem | −77.0% | n = 6 |
| Untreated Controls | +0.7% | n = 6 |
| A | −63.0% | n = 3 |
| B | −26.8% | n = 6 |
| C | −22.1% | n = 4 |
| D | −16.5% | n = 2 |
| E | −13.0% | n = 2 |
| F | −9.1% | n = 3 |
| G | −8.4% | n = 2 |
| H | −5.6% | n = 2 |

In the table above, compound A, for example, inhibited contracture by -63.0% at 2mM Ca++ as compared to the control. That is, compound A inhibited almost two thirds of the contracture observed for the control at 2mM Ca++. As used above, compounds A, B, C, D, E, F, G and H are as follows:

A is (+)-cis-6-(Acetyloxy)-6,7-dihydro-7-(4-methoxyphenyl) 4-[2-(dimethylamino)ethyl]-3-phenyl-1,4-thiazepin-5-(4H)-one hydrochloride;

B is cis-rac.6-(Acetyloxy)-6,7-dihydro-7-(4-methoxyphenyl) -4-[2-(dimethylamino)ethyl]-3-phenyl-1,4-thiazepin-5(4H)-one hydrochloride;

C is cis-rac.6,7-Dihydro-6-methoxy-7-(4-methoxyphenyl)-4[2-(dimethylamino)ethyl-3-phenyl-1,4-thiazepin-5(4H)-one hydrochloride;

D is cis-rac.-6,7-Dihydro-6-hydroxy-7-(4-methoxyphenyl)-4[2-(dimethylamino)ethyl]-3-phenyl-1,4-thiazepin-5(4H)-one hydrochloride;

E is cis-(+)-6,7-Dihydro-6-hydroxy-7-(4-methoxyphenyl)-4[2-(dimethylamino)ethyl-3-phenyl-1,4-thiazepin-5(4H)-one (E)-2-butenedioate;

F is (-)-cis-6-(Acetyloxy)-6,7-dihydro-7-(4-methoxyphenyl) -4-[2-(dimethylamino)ethyl]-3-phenyl-1,4-thiazepin-5 (4H)-one [S-(R,* R,*)]-2,3-dihydroxybutanedioic acid salt;

G is trans-rac.-6-(Acetyloxy)-6,7-dihydro-7-(4-methoxy-phenyl)-4-[2-(dimethylamino)ethyl]-3-phenyl-1,4-thiazepin-5(4H)-one hydrochloride; and H is trans-rac.-6,7-Dihydro-6-hydroxy-7-(4-methoxyphenyl) -4-[2-(dimethylamino)ethyl]-3-phenyl-1,4-thiazepin-5 (4H)-one (E)-2-butenedioate.

As shown above, all of the compounds of the invention that were tested showed activity in the above test. The compounds of formula I, and the pharmaceutically acceptable acid addition salts thereof, as herein described, can be incorporated into standard pharmaceutical dosage forms. The compounds of formula I are useful for oral or parenteral application with the usual pharmaceutical carrier materials, for example, organic or inorganic inert carrier materials, such as water, gelatin, lactose, starch, magnesium stearate, talc, vegetable oils, gums, polyalkylene glycols, and the like. The pharmaceutical preparations can be employed in a solid form, for example, as tablets, or capsules, or in liquid form, for example as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The invention also relates to a method of inducing calcium antagonist activity in a warm-blooded animal in need such treatment which comprises administering an effective amount of a compound of formula I. The invention also relates to a method of lowering blood pressure or treating ischemia by bringing about myocardial preservation during ischemia, which comprises administering an effective amount of a compound of formula I, or pharmaceutically acceptable acid addition salts thereof to a warm-blooded animal in need of such treatment. The amount of an oral daily dosage can be determined by one skilled in the art and would be comparable to that of diltiazem. The amount of an intravenous dosage can also be determined by one skilled in the art and is comparable to that of diltiazem. It is to be understood, however, that dosages may vary from individual to individual, and accordingly the above recitation is not intended to limit the scope of the present invention in any way.

The following examples further illustrate the invention. All temperatures are in degrees Celsius, unless otherwise mentioned.

EXAMPLE 1

3-(4-Methoxyohenyl)oxiranecarboxamide

A mixture of 20.0 g (0.096 mol) of trans-3-(p-methoxyphenyl)glycidate and 200 mL of concentrated ammonium hydroxide was stirred at room temperature for 6 hrs. The product was separated by filtration, washed with water and air dried. It was suspended in 150 mL of ether, stirred at room temperature for 2 hrs and filtered to give 15.5 g (84%) of 3-(4-methoxyphenyl)oxiranecarboxamide, mp 65°-167°.

EXAMPLE 2 rac.-(R,*S*)- and (R,*R*)-αHydroxy-4-methoxyohenyl-β-[(2-oxo-2-phenylethyl)thio]-benzenepropanamide To a solution of 8.1 g (0.053 mol) of 2-mercapto-1-phenylethanone in 100 mL of toluene under nitrogen was added 10.2 g (0.053 mol) of 3-(4-methoxyphenyl-)oxiranecarboxamide and the mixture was stirred and heated in an oil bath at 120o for 3 hrs. The solvent was removed under reduced pressure to give 18.1 g of crude product, which was dissolved in a minimum amount of a mixture of methylene chloride--ethyl acetate (8:2) and chromatographed using a Waters Prep. LC-system 500 A. Eluted with the same solvents and 200 mL fractions were collected. Fractions 18-21 provided 9.3 g of crude product of which was rechromatographed using ethyl acetate--hexane (75:25) as elutants. Fraction 7 after removal of the solvent yielded a residue, which after crystallization from ethyl acetate gave 0.9 g (5%) of rac.-(R,*R*)-α-hydroxy-4-methoxyphenyl-β-[ (2-oxo-2-phenylethyl)thio]benzenepropanamide, mp 132°–134°.

The column was continued eluting with the same solvent system. Fractions 12-20 were collected and after removal of the solvent at reduced pressure yielded 3.8 g of crude product, of 85% purity by NMR. This compound was further purified by column chromatography using 76g of silica gel. Elution was with ethyl acetate; 20 mL fractions were collected. Fractions 1-23 containing the pure product were combined and concentrated under reduced pressure to give 3.6 g (20%) of rac.-(R,*S*)-β-hydroxy-4-methoxyphenyl-β-[(2-oxo-2-phenylethyl)thio]benzenepropanamide as an amorphous substance.

EXAMPLE 3 rac.-(R,*R*)-β-Hydroxy-4-methoxyohenyl-β-[(2-oxo-2 -phenylethyl)thio1benzenepropanamide To a solution of 8.0 g (0.052 mol) of 2-mercapto-1-phenylethanone in 120 mL of acetonitrile was added 0.3 g (0.052 mol) of powdered potassium carbonate and 10.1 g (0.052 mol) of 3-(4-methoxyphenyl)oxiranecarboxamide. After the mixture was stirred and heated at reflux under nitrogen for 3.5 hours the solvent was removed under reduced pressure. The crude product was chromatographed on silica gel (150 g). The column was eluted with ethyl acetate, fractions 7-13 containing the product were combined and the solvent was removed under reduced pressure. The residue was crystallized from ethyl acetate to give 4.0 g (22%) of rac.-(R,*R*)-α-hydroxy-4-methoxyphenyl- β-[(2-oxo-2 -phenylethyl)thio]benzenepropanamide, mp 132°–134°.

EXAMPLE 4 rac.-(S,*R*)-α-(Acetyloxy)-4-methoxyohenyl-β-[(2-oxo-2 -phenylethyl)thio]benzenepropanamide To a solution of 3.5 g (0.01 mol) of rac.-(R,*S*)α-(hydroxy)-4-methoxyphenyl-β-[(2-oxo -2-phenYlethYl)thio]benzenepropanamide in 130 mL of methylene chloride and 4.4 mL of pyridine was added dropwise at ice-bath temperature a solution of 1.1 g (0.014 mol) of acetyl chloride in 25 mL of methylene chloride. The mixture was stirred at this temperature for one hour then at room temperature for 17 hrs and diluted with water. The aqueous suspension was extracted with methylene chloride and the combined organic solutions were washed with water and dried (MgSO$_4$). Removal of the solvent gave the crude ester, which after crystallization from ethyl acetate afforded 2.9 g (74%) of rac.-(S,*R*)-α-(acetyloxy)-4-methoxyphenyl -β-[(2-oxo-2-phenylethyl) thio]benzenepropanamide, mp 122°–123°.

EXAMPLE 5 rac.-(S,*S*)-6-(Acetyloxy)-6.7-dihydro-7-(4-methoxy phenyl)-3-phenyl-1.4-thiazepin-5(4H)-one A mixture of 0.5 g (0.0013 mol) of rac.-(S,*R*)-α-(acetyloxy)-4-methoxyphenyl-β-[(2-oxo-2-phenylethyl) thio]benzenepropanamide, 0.059 g of p-toluenesulfonic acid in 20 mL of toluene was stirred and heated at reflux for 20 hrs, while the water formed was removed with the aid of a Dean-Stark trap. The solvent was removed under reduced pressure and the residue was crystallized from acetone--ether to afford 0.2 g (43%) of rac.-(S,*S*)-6-(acetyloxy)-6,7-dihydro-7-(4-methoxy phenyl)-3-phenyl-1,4-thiazepin-5(4H)-one, mp 225°–226°.

EXAMPLE 6 rac.-(R,*R*)-α-(Acetyloxy)-4-methoxyohenyl-β-[(2-oxo-2-phenylethyl) thio]benzenepropanamide To a mixture of 4.0 g (0.0116 mol) of rac.-(R, R*)-α-hydroxy-4-methoxyphenyl-β-[(2-oxo-2-phenylethyl) thio]benzenepropanamide, 130 mL of methylene chloride and 5 mL of pyridine cooled in an ice-bath was added dropwise a solution of 1.25 g (0.0126 mol) of acetyl chloride in 25 mL of methylene chloride. The mixture was stirred at this temperature for one hour and at room temperature for 17 hours. After dilution with water the aqueous suspension was extracted with methylene chloride. The methylene chloride solution was dried (MgSO$_4$) and removal of the solvent gave a residue which was washed with hexane. The crude product was crystallized from ethyl acetate to give 4.1 g (93%) of rac.-(R,*R*)-α-(acetyloxy)-4-methoxyphenyl-β-[(2-oxo-2-phenylethyl)thio]benzeneprop anamide, mp 154°–155°.

EXAMPLE 7 rac.-trans-6-(Acetyloxy)-6.7-dihydro-7-(4-methoxyohenyl) -3-phenyl-1,4-thiazepin-5(4H)-one A mixture of 1.0 g (0.003 mol) of rac.-(R,*R*)-α-(acetyloxy)-4-methoxyphenyl-β-[(2-oxo-2 -phenylethyl)thio]benzenepropanamide, 0.1 g of p-toluenesulfonic acid in 50 mL toluene was stirred and heated at reflux for 6 hrs while the water formed was removed with the aid of a Dean-Stark trap. The solvent was removed under reduced pressure and the residue was chromatographed on 15 g of silica gel. The column was eluted with ethyl acetate--methylene chloride (10:90) and fractions 26-30 containing the product were combined and concentrated under reduced pressure to give 0.2 g (21%) of rac.-trans-6-(acetyloxy)-6,7-dihydro-7-(4-methoxyphenyl) -3-phenyl-1,4-thiazepin-5(4H)-one. Analytical sample was recrystallized from ethanol, mp. 225°–226°.

EXAMPLE 8 rac.-Cis-6-(Acetyloxy)-6,7-dihydro-7-(4-methoxyphenyl)-4 -[2-(dimethylamino)ethyl]-3-phenyl-1,4-thiazepin-5(4H)-one A mixture of 3.9 g (0.01 mol) of rac.-cis-6-(acetyloxy)-6,7-dihydro-7-(4-methoxyphenyl)-1, 4-thiazepin-5(4H)-one, 1.5 g of powdered potassium carbonate and 1.3 g (0.011 mol) of 2-dimethylaminoethyl chloride in 100 mL of ethyl acetate was stirred and heated at reflux for 2 hrs, then twice an additional 0.5 g of 2-dimethylaminoethyl chloride was added at 2 hr intervals. The mixture was heated at reflux for a total of 12 hrs, cooled to room temperature and diluted with water. The organic solution was separated, washed with brine, dried (MgSO$_4$) and the solvent was removed under reduced pressure. The residue in acetone was treated with hydrogen chloride (anhydrous) and the crude hydrochloride salt after recrystallization from acetone afforded 4.0 g (80%) of rac.-cis-6-(acetyloxy)-6,7-dihydro-7-(4-methoxyphenyl)-4 -[2-(dimethylamino)ethyl]-3-phenyl-1,4-thiazepin-5(4H)-one hydrochloride, mp 125°–127°.

The above hydrochloride, 4.0 g (0.008 mole) in water was treated with ammonium hydroxide and the aqueous suspension was extracted with methylene chloride. The methylene chloride solutions were dried (MgSO$_4$) and removal of the solvent gave 3.6 g (97%) of rac.-cis-6-(acetyloxy)-6,7-dihydro-7-(4-methoxyphenyl)-4-[2-(dimethylamino)-ethyl]-3-phenyl-1 , 4-thiazepin-5(4H)-one. Analytical sample was recrystallized from ether, mp 115°-116°.

EXAMPLE 9 rac.-cis-6,7-Dihydro-6-hydroxy-7-(4-methoxyohenyl)-4-[2-(dimethylamino) ethyl]-3-phenyl-1,4-thiazepin-5(4H)-one A mixture of 0.5 g (0.001 mol) of rac-cis-6-(acetyloxy)-6,7-dihydro-7-(4-methoxyphenyl)-4[2-(dimethylamino)ethyl]-3-phenyl-1,4-thiazepin-5(4H)-one and 5 mL of ethyl acetate saturated with hydrogen chloride was stirred at room temperature for 17 hours. The solvent was removed under reduced pressure and the residue was partitioned between water and ammonium hydroxide. The ethyl acetate solution was washed with brine, dried (MgSO$_4$) and removal of the solvent gave 0.3 g (67%) of rac.-cis-6,7-dihydro-6-hydroxy-7-(4-methoxyphenyl)-4-[2(dimethylamino) ethyl]-3-phenyl-1,4-thiazepin-5(4H)-one. Analytical sample was crystallized from ethyl acetate, mp 159°-160°.

The above base, 0.3 g (0.001 mol) in acetone was treated with hydrogen chloride (anhydrous) to give 0.2 g (63%) of rac.-cis-6,7-dihydro-6-hydroxy-7(4-methoxyphenyl)-4-[2-(dimethylamino)ethyl]-3-phenyl-1, 4-thiazepin-5(4H)-one hydrochloride, mp 180°-181°.

EXAMPLE 10 rac.-cis-6,7-Dihydro-6-methoxy-7-(4-methoxyphenyl)-4-[2(dimethylamino) ethyl]-3-phenyl-1,4-thiazepin-5(4H)-one To a mixture of 2.8 g (0.007 mol) of rac.-cis-6,7-dihydro-6-hydroxy-7-(4-methoxyphenyl)-4-[2-(dimethylamino) ethyl]-3-phenyl-1,4-thiazepin-5(4H)-one in 60 mL benzene (dry), 0.5 g of sodium hydride (50% dispersion in mineral oil) was added and the mixture was heated at reflux for one hour. After cooling 1.3 g (0.01 mol) of dimethyl sulfate was added dropwise to the above mixture and stirred at room temperature for 17 hours. The reaction mixture was diluted with water and the aqueous suspension was extracted with ethyl acetate. The combined ethyl acetate solutions were washed with brine, dried (MgSO$_4$) and removal of the solvent gave after recrystallization from ethyl acetate, 1.2 g (42%) of rac.-cis-6,7-dihydro-6-methoxy-7-(4-methoxyphenyl)-4-[2-(dimethylamino)ethyl]-3-phenyl-1,4-thiazepin-5(4H)-one, mp 133°-135°.

The above base, 1.2 g (0.003 mol) in acetone was treated with hydrogen chloride (anhydrous) to give, after recrystallization from acetone, 1.2 g (92%) of rac.-cis-6,7-dihydro-6-methoxy-7-(4-methoxyphenyl)-4-[2-(dimethylamino) ethyl]-3-phenyl-1,4-thiazepin-5(4H)-one hydrochloride, mp 151°-153°.

EXAMPLE 11 rac.-trans-6-(Acetyloxy)-6,7-dihydro-7-(4-methoxyohenyl) -4-[2-(dimethylamino)ethyl]-3-phenyl-1,4-thiazepin-5(4H) -one A mixture of 1.1 g (0.003 mol) of rac.-trans-6-(acetyloxy)-6,7-dihydro-7-(4-methoxyphenyl) -3-phenyl-1,4-thiazepin-5(4H)-one, 0.5 g of potassium carbonate (powdered) and 0.3 g (0.003 mol) of 2-dimethylaminoethyl chloride in 25 mL of ethyl acetate was stirred and heated at reflux for 2 hrs, then twice an additional 0.15 g of 2-dimethylaminoethyl chloride was added at 2 hr intervals. The mixture was heated at reflux for a total of 12 hrs., cooled to room temperature and diluted with water. The aqueous suspension was extracted with ethyl acetate then the organic solution was washed with brine and dried (MgSO$_4$). Removal of the solvent gave 1.2 g (92%) of rac.-trans-6-(acetyloxy)-6,7-dihydro-7-(4-methoxyphenyl) -4-[2-(dimethylamino)ethyl]-3-phenyl-1,4-thiazepin-5(4H) -one. Analytical sample was recrystallized from ether, mp 147°-148°.

A sample of the above base, in ethyl acetate on treatment with hydrogen chloride (anhydrous) gave after recrystallization from acetone rac.-trans-6-(acetyloxy)-6,7-dihydro-7-(4-methoxyphenyl) -4-[2-(dimethylamino)ethyl]-3-phenyl-1,4-thiazepin-5(4H) -one hydrochloride, mp 150°-151°.

EXAMPLE 12 rac.-trans-6,7-Dihydro-6-hydroxy-7-(4-methoxyohenyl)-4[2-(dimethylamino)ethyl]-3-phenyl1-1,4-thiazepin-5{4H)-one A mixture of 0.5 g (0.0001 mol) of rac.-trans-6-(acetyloxy)-6,7-dihydro-7-(4-methoxyphenyl) -4-[2-(dimethylamino)ethyl]-3-phenyl-1,4-thiazepin-5(4H) -one, 10 mL 0.5M of aqueous potassium carbonate in 15 mL of ethyl acetate was stirred at room temperature for 45 minutes and heated at 50°-60° for 2 hrs. The mixture was poured onto brine and the aqueous suspension was extracted with ethyl acetate. The organic solutions were washed with brine and dried (MgSO$_4$). Removal of the solvent gave after recrystallization from ethyl acetate 0.3 g (67%) of rac.-trans-6,7-dihydro-6-hydroxy-7-(4-methoxyphenyl)-4[2-(dimethylamino)ethyl]-3-phenyl-1,4-thiazepin-5(4H)-one, mp 147°-148°.

The above base, 0.2 g (0.0005 mol) in acetone (5 mL) was combined with 0.06 g of fumaric acid then heated until solution occurred and allowed to stand at room temperature overnight. The crystals were separated by filtration and dried to afford 0.2 g (80%) of trans-rac.-6,7-dihydro-6-hydroxy -7-(4-methoxyphenyl)-4-[2-(dimethylamino)ethyl]-3-phenyl-1, 4-thiazepin-5(4H)-one (E)-2-butenedioate, mp 150°-152°.

EXAMPLE 13

Resolution of (±)-cis-6-(AcetyloxY)-6,7-dihydro-7-(4-methoxyohenyl) -4-[2-(dimethylamino)ethyl]-3-phenyl-1,4-thiazepin-5(4H)-one A hot solution of 12.5 g (0.028 mol) of rac.-cis-(6-acetyloxy)-6,7-dihydro-7-(4-methoxyphenyl) -4-[2-(dimethylamino)ethyl]-3-phenyl-1,4-thiazepin-5(4H) -one in 110 mL of ethanol was combined with a hot solution of 4.25 g (0.028 mol) of d-tartaric acid in 60 mL ethanol. The clear solution was seeded with a few crystals of (−)B.d-TA and allowed to crystallize at room temperature for 18 hrs. The crystals were separated by filtration and dried to yield 14.1 g of crude product. After one recrystallization from methanol (200 mL) yielded 6.1 g (73%) of pure (−)-cis-6-(acetyloxy)-6,7-dihydro-7-(4-methoxyphenyl) -4-[2-(dimethylamino)ethyl]-3-phenyl-1,4-thiazepin-5(4H)-one [S-(R*, R*)]-2,3- dihydroxybutanedioic acid salt, mp 201°-203°, [α]25 −82.66° (C 1.02, MeOH).

EXAMPLE 14

(−)-cis-6-(Acetyloxy)-6,7-dihydro-7-(4-methoxyohenyl)-4[2-(dimethylamino)ethyl]1 1-3-phenyl-1,4-thiazepin-5(4H)-one (−)-cis-6-(Acetyloxy)-6,7-dihydro-7-(4-methoxyphenyl)-4-[2-(dimethylamino)ethyl]-3-phenyl-1,4-thiazepin-5(4H)-one [S-(R,*R)]-2,3-dihydrobutanedioic acid salt, 5.3 g (0.009 mol) in 60 mL of water was decomposed with concentrated ammonium hydroxide. The resulting suspension was extracted with methylene chloride (3×100 mL). The combined methylene chloride solutions were washed with water (50 mL) and dried (MgSO4). Removal of the solvent gave 3.9 g (99%) of (−)-cis-6-(acetyloxy)-6,7-dihydro-7-(4-methoxyphenyl)-4-[2-(dimethylamino)ethyl]-3-phenyl-1, 4-thiazepin-5(4H)-one, mp 149°-151°, [α]25 −156.63° (C 1.05, MeOH).

The above base, 3.8 g (0.009 mol) on treatment with hydrogen chloride (anhydrous) in ethyl acetate gave the crude hydrochloride, which after recrystallization from acetone afforded 3.9 g (95%) of (−)-cis-6-(acetyloxy)-6,7-dihydro-7-(4-methoxyphenyl)-4[2-(dimethylamino)ethyl]-3-phenyl-1,4-thiazepin-5(4H)-one hydrochloride, mp 234°-236°, [α]25 −105.57° (C 0.96, MeOH).

EXAMPLE 15

(+)-cis-6-(Acetyloxy)-6,7-dihydro-7-(4-methoxyohenyl)-4[2-(dimethylamino)ethyl]-3-phenyl-1,4-thiazepin-5(4H)-one [R-(R*,R*)]-2,3-Dihydroxybutanedioic Acid Salt The combined mother liquors obtained in the preparation of (−)-base, [S-(R*,R*)]-2,3dihydroxybutanedioate were concentrated to dryness. The residue in water was decomposed with concentrated ammonium hydroxide and the resulting suspension was extracted with methylene chloride (3×200 mL). The combined extracts were dried (MgSO4) and removal of the solvent gave 7.1 g (0.016 mol) of crude (+)-cis-6-(acetyloxy)-6, 7-dihydro-7-(4-methoxyphenyl)-4-(2-dimethylamino) ethyl]-3-phenyl-1,4-thiazepin-5(4H)-one. The crude base, 7.1 g (0.016 mol) was dissolved in 65 mL of hot ethanol and combined with a hot solution of 2.4 g (0.016 mol) of l-tartaric acid in 32 mL hot ethanol. The solution was seeded with a few crystals of (+)B.L-TA and allowed to crystallize at room temperature overnight. The crystals were collected by filtration and dried to give 6.6 g of crude product, mp 197°-198°. The recrystallization from methanol (75 mL) yielded 5.8 g (70%) of pure (+)-cis-6-(acetyloxy)-6,7-dihydro-7-(4-methoxyphenyl)-4[2-(dimethylamino)ethyl]-3-phenyl-1,4-thiazepin-5(4H)-one [R-(R*, R*)]-2,3-dihydrobutanedioic acid salt, mp 201°-203°, [α]25 +88.63° (C 0.99, MeOH).

EXAMPLE 16

(+)-cis-6-(Acetyloxy)-6,7-dihydro-7-(4-methoxyohenyl)-4[2-(dimethylamino)ethyl]-3-phenyl-1,4-thiazepin-5(4H)-one (+)-cis-6-(Acetyloxy)-6,7-dihydro-7-(4-methoxyphenyl)-4-[2-(dimethylamino)ethyl]-3-phenyl-1,4-thiazepin-5(4H)-one [R-(R*, R*)]-2,3-dihydroxybutanedioate, 5.8 g (0.01 mol) in 60 mL water was decomposed with concentrated ammonium hydroxide. The resulting suspension was extracted with methylene chloride (3×100 mL). The combined methylene chloride solutions were dried (MgSO4) and removal of the solvent gave 3.7 g (86%) of (+)-cis-6-(acetyloxy)-6, 7-dihydro-7-(4-methoxyphenyl)-4-[2-(dimethylamino) ethyl]-3-phenyl-1,4-thiazepin-5(4H)-one. Analytical sample was recrystallized from ether, mp 149°-151°, [α]25 +158.89° (C 0.55, MeOH).

The above base, 3.7 g (0.008 mol) on treatment with hydrogen chloride (anhydrous) in ethyl acetate gave after recrystallization from acetone 3.75 g (94%) of (+)-cis-6,7-Dihydro-6-hydroxy-7-(4-methoxyohenyl)-4-[2(dimethylamino) ethyl]-3-phenyl-1, 4-thiazepin-5(4H)-one hydrochloride, mp 234°-236°, [α]25 +103.18° (C 1.02, MeOH).

EXAMPLE 17

(+)-cis-6,7-Dihydro-6-hydroxy-7-(4-methoxyphenyl)-4-l -[

A mixture of 1.3 g (0.003 mol) of (+)-cis-6-(acetyloxy)-6,7-dihydro-7-(4-methoxyphenyl)-4[2-(dimethylamino)ethyl]-3-phenyl-1,4-thiazepin-5(4H)-one and 30 mL 0.5 M potassium carbonate in 45 mL ethanol was stirred at room temperature for one hour. The solvent was removed under reduced pressure and the residue was partitioned between water and ethyl acetate. The ethyl acetate solution was washed with brine and dried (MgSO4). Removal of the solvent gave the crude base, which after recrystallization from ether afforded 1.1 g (94%) of (+)-cis-6,7-dihydro-6-hydroxy-7-(4-methoxyphenyl)-4-[2 -(dimethylamino)ethyl]-3-phenyl-1,4-thiazepin-5(4H)-one, mp 110°-112°, [α]25 +122.72° (C 1.01, MeOH).

The above base, 0.3 g (0.0008 mol) on treatment with fumaric acid (0.09 g) in acetone gave the crude salt, which after recrystallization from acetone afforded 0.3 g (78%) of (+)-cis-6,7-dihydro-6-hydroxy-7-(4-methoxyphenyl)-4-[2-(dimethylamino)ethyl]-3- phenyl-1, 4-thiazepin-5(4H)-one (E)-2-butenedioate, mp 154°-155°, [α]25 +65.38° (C 1.00,MeOH).

EXAMPLE 18

(−)-cis-6,7-Dihydro-6-hydroxy-7-(4-methoxyphenyl)-4-[2-(dimethylamino) ethyl]-3-phenyl-1,4-thiazepin-5(4H)-one A mixture of 1.2 g (0.003 mol) of (−)-cis--6-(acetyloxy)-6,7-dihydro-7-(4-methoxyphenyl)-4[2-(dimethylamino)ethyl)-3-phenyl-1,4-thiazepin-5(4H)-one and 30 mL 0.5M potassium carbonate in 45 mL ethanol was stirred at room temperature for one hour. The solvent was removed under reduced pressure and the residue was partitioned between water and ethyl acetate. The ethyl acetate solution was washed with brine and dried (MgSO4). Removal of the solvent gave the crude base, which after recrystallization from ether afforded 1.1 g (100%) of (−)-cis-6,7-dihydro-6-hydroxy-7-(4-methoxyphenyl)-4-[2(dimethylamino)ethyl]-3-phenyl-1,4-thiazepin-5(4H)-one, mp 110°-112°, [α]25 −115.36° (C 0.99, MeOH).

The above base, 23.03 g (0.0008 mol) on treatment with fumaric acid (0.09 g) in acetone gave the crude salt, which after recrystallization from acetone afforded 0.35 g (92%) of (-)-cis-6,7-dihydro-6-hydroxy-7-(4-methoxyphenyl)-4-[2-(dimethylamino)ethyl]-3-phenyl-1,4-thiazepin-5(4H)-one (E)-2-butenedioate, mp 155°-156°, 25 −64.73° (C 1.05, MeOH).

EXAMPLE 19

| Parenteral Solution | | |
|---|---|---|
| Item | Ingredient | mg/ml |
| 1. | Compound A | 10 |
| 2. | Benzyl Alcohol | 10 |
| 3. | Sorbitol | 38 |
| 4. | Hydrochloric Acid U.S. to pH | 3–7 |
| 5 | Sodium Hydroxide q.s. to pH | 3–7 |
| 6. | Water for Injection q.s. to | 1 ml |

EXAMPLE 20

| Capsule | mg/Capsule | |
|---|---|---|
| Item Ingredient | 100 mg. | 200 mg |
| 1. Compound B | 100 | 200 |
| 2. Corn Starch (Pregelatinized) | 50 | 80 |
| 3. Modified Starch | 10 | 20 |
| 4. Talc | 20 | 20 |
| 5. Magnesium Stearate | 1 | 1 |
| | 181 mg | 322 mg |

(1) Mix items 1–3 and wet granulate with water. Dry at 45° overnight.
(2) Mill through suitable screen using appropriate milling equipment.
(3) Add items (4) and (5) and mix for five minutes.
(4) Fill into suitable capsule.

As used herein, compounds A and B are as designated in the specification above.

We claim:

1. A compound of the formula

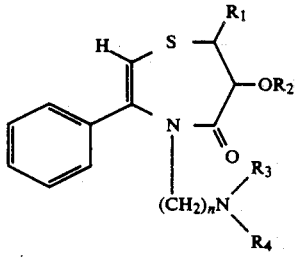

I wherein $R_1$ is phenyl substituted with 1 to 3 substituents selected from the group consisting of halogen and lower alkoxy; $R_2$ is hydrogen, lower alkyl, lower alkanoyl, lower cycloalkanoyl,

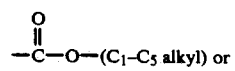

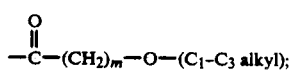

$R_3$ and $R_4$ are independently lower alkyl, phenyl lower alkyl or together form a piperidine or pyrrolidine ring; n is 2 to 4; m is 1 to 2; or a pharmaceuticallY acceptable acid addition salt thereof, with the priviso that when $R_1$, is 4-methoxyphenyl, $R_2$ is hydrogen, and $R_3$ and $R_4$ are methyl; and n is 2, the compound of formula I cannot be in the (−)-cis form.

2. A compound in accordance with claim 1, of the formula

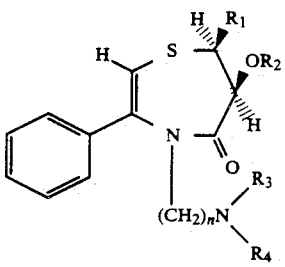

I' wherein $R_1$ is phenyl substituted with 1 to 3 substituents selected from the group consisting of halogen and lower alkoxy; $R_2$ is hydrogen, lower alkyl, lower alkanoyl, lower cycloalkanoyl,

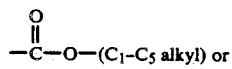

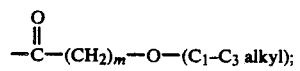

$R_3$ and $R_4$ are independently lower alkyl, phenyl lower alkyl or together form a piperidine or pyrrolidine ring; n is 2 to 4; m is 1 to 2; an enantiomer or a racemate thereof or a pharmaceutically acceptable acid addition salt thereof.

3. A compound in accordance with claim 1, of the formula

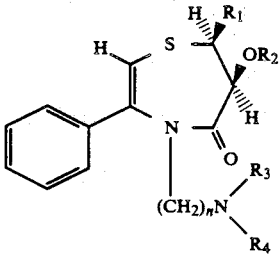

I' wherein $R_1$ *is phenyl substituted with* 1 to 3 substituents selected from the group consisting of halogen and lower alkoxy; $R_2$ is hydrogen, lower alkyl, lower alkanoyl, lower cycloalkanoyl,

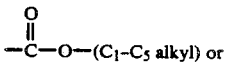

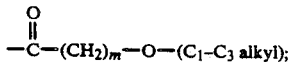

$R_3$ and $R_4$ *are independently lower alkyl, phenyl lower alkyl or together form a piperidine or pyrrolidine ring*; n *is* 2 to 4; m is 1 to 2; or a pharmaceutically acceptable acid addition salt thereof.

4. A compound in accordance with claim 3 wherein $R_1$ is 4-lower alkoxyphenyl, $R_2$ is lower alkanoyl, $R_3$ and $R_4$ are independently lower alkyl and n is 2 to 3.

5. A compound in accordance with claim 4, (+)-cis-6-(acetyloxY)-6,7-dihydro-7-(4-methoxyphenyl)-4-[2dimethylamino)ethyl]-3-phenyl-1,4-thiazepin-5(4H)-one, or the hydrochloride salt thereof, or the [R-(R*, R)]-2,3-dihydroxy butanedioic acid salt thereof.

6. A compound in accordance with claim 3, (+)-cis-6,7-dihydro-6-hydroxY-7-(4-methoxyphenyl)-4[2-(dimethylamino)ethyl]-3-phenyl-1,4-thiazepin-5(4H)-one or the (E)-2-butenedioate salt thereof.

7. A compound in accordance with claim 2 wherein $R_1$ is 4-lower alkoxyphenyl, R2 is lower alkanoyl, $R_3$ and $R_4$ are independently lower alkyl and n is 2 to 3.

8. A compound in accordance with claim 7, cis-rac.-6-(acetyloxy)-6,7-dihydro-7-(4-methoxyphenyl)-4-[2(dimethYlamino)ethyl]-3-phenyl-1,4-thiazepin-5(4H)-one, or the hydrochloride salt thereof.

9. A compound in accordance with claim 2 wherein $R_1$ is 4-lower alkoxyphenyl, $R_2$ is hydrogen, $R_3$ and $R_4$ are independently lower alkyl and n is 2 to 3.

10. A compound in accordance with claim 9, cis-rac.-6,7-dihydro-6-hydroxy-7-(4-methoxyphenyl)-4[2-(dimethylamino)ethyl]-3-phenyl-1,4-thiazepin-5(4H)-one, or the hydrochloride salt thereof.

11. A compound in accordance with claim 2, cis-rac.-6,7-dihydro-6-methoxy-7-(4-methoxyphenyl)-4-[2(dimethylamino)ethyl]-3-phenyl-1,4-thiazepin-5(4H)-one, or the hydrochloride salt thereof.

12. A compound in accordance with claim 2, (-)-cis-6-(acetyloxy)-6,7-dihydro-7-(4-methoxyphenyl)-4-[2(dimethylamino)ethyl]-3-phenyl-1,4-thiazepin-5(4H)-one, or the hydrochloride salt thereof.

13. A compound in accordance with claim 1, of the formula

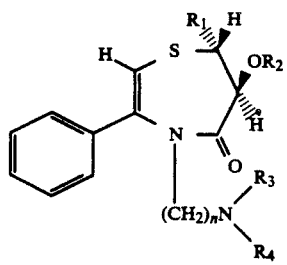

I''' wherein $R_1$ is phenyl substituted with 1 to 3 substituents selected from the group consisting of halogen and lower alkoxy; $R_2$ is hydrogen, lower alkyl, lower alkanoyl, lower cycloalkanoyl,

—C—O—($C_1$-$C_5$ alkyl) or

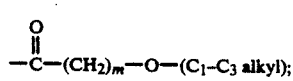

—C—($CH_2$)$_m$—O—($C_1$-$C_3$ alkyl);

$R_3$ and $R_4$ are independently lower alkyl, phenyl lower alkyl or together form a piperidine or pyrrolidine ring; n is 2 to 4; m is 1 to 2; an enantiomer or racemate thereof or a pharmaceutically acceptable acid addition salt thereof.

14. A compound in accordance with claim 13, wherein $R_1$ is 4-lower alkoxyphenyl, $R_2$ is lower alkanoyl, $R_3$ and $R_4$ are independently lower alkyl and n is 2 to 3.

15. A compound in accordance with claim 14, trans-rac.-6-(acetyloxy)-6,7-dihydro-7-(4-methoxyphenyl)-4-[2(dimethylamino)ethyl]-3-phenyl-1,4-thiazepin-5(4H)-one or the hydrochloride salt thereof.

16. A compound in accordance with claim 13 wherein $R_1$ is 4-lower alkoxyphenyl, $R_2$ is hydrogen, $R_3$ and $R_4$ are independently lower alkyl and n is 2 to 3.

17. A compound in accordance with claim 16, trans-rac.-6,7-Dihydro-6-hydroxy-7-(4-methoxyphenyl)-4[2-(dimethylamino)ethyl]-3-phenyl-1,4-thiazepin-5(4H)-one or the (E)-2-butenedioate salt thereof.

18. A calcium channel blocking composition comprising an effective amount of a compound of the formula

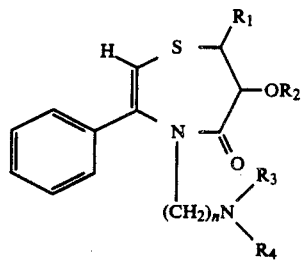

I wherein $R_1$ is phenyl substituted with 1 to 3 substituents selected from the group consisting of halogen and lower alkoxy; $R_2$ is hydrogen, lower alkyl, lower alkanoyl, lower cycloalkanoyl,

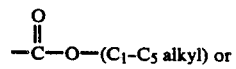

—C—O—($C_1$-$C_5$ alkyl) or

—C—($CH_2$)$_m$—O—($C_1$-$C_3$ alkyl);

$R_3$ and $R_4$ are independently lower alkyl, phenyl lower alkyl or together form a piperidine or pyrrolidine ring; n is 2 to 4; m is 1 to 2; with the priviso that when $R_1$ is 4-methoxyphenyl, $R_2$ is hydrogen and $R_3$ and $R_4$ are methyl; and n is 2, the compound of formula I cannot be in the (—)-cis form, or a pharmaceutically acceptable acid addition salt thereof and a pharmaceutically inert carrier material.

19. A composition in accordance with claim 18, wherein $R_1$ is 4-lower alkoxyphenyl, $R_2$ is lower alkanoyl, $R_3$ and $R_4$ are independently lower alkyl and n is 2 to 3.

20. A composition in accordance with claim 19 wherein the compound of formula I is (+)-cis-rac.-6-(acetyloxy)-6,7-dihydro-7-(4-methoxyphenyl)-4-[2-(dimethylamino)-ethyl]-3-phenyl-1,4-thiazepin-5(4H)-one, the hydrochloride salt thereof, or the [R-(R*, R)]-2,3-dihydroxy butanedioic acid salt thereof.

21. A method of inducing calcium channel blockage, which comprises administering to a warm-blooded animal in need of such treatment an effective amount of a compound of the formula

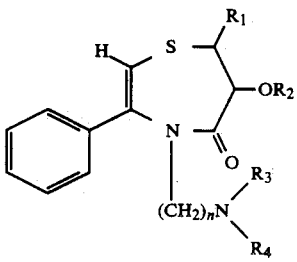

wherein $R_1$ is phenyl substituted with 1 to 3 substituents selected from the group consisting of halogen and lower alkoxy; $R_2$ is hydrogen, lower alkyl, lower alkanoyl, lower cycloalkanoyl,

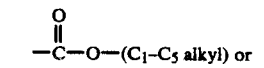

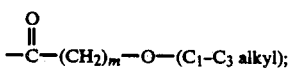

$R_3$ and $R_4$ are independently lower alkyl, phenyl lower alkyl or together form a piperidine or pyrrolidine ring; n is 2 to 4; m is 1 to 2; or a pharmaceutically acceptable acid addition salt thereof, with the proviso that when $R_1$ is 4-methoxyphenyl, $R_2$ is hydrogen and $R_3$ and $R_4$ are methyl; and n is 2, the compound of formula I cannot be in the (−)-cis form.

22. A method in accordance with claim 21 wherein $R_1$ is 4-lower alkoxyphenyl, $R_2$ is lower alkanoyl, $R_3$ and $R_4$ are independently lower alkyl, and n is 2 to 3.

23. A method in accordance with claim 22, wherein the compound of formula I is (+)-cis-rac.-6-(acetyloxy)-6,7-dihydro-7-(4-methoxyphenyl) -4-[2-(dimethylamino)-ethyl]-3-phenyl-1,4-thiazepin-5(4H)-one, the hydrochloride salt thereof, or the [R-(R*, R)]-2,3-dihydroxybutanedioic acid salt thereof.

24. A compound of the formula

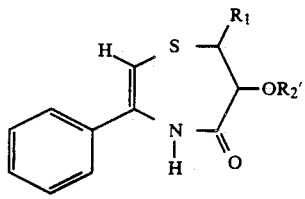

wherein $R_1$ is phenyl substituted with 1 to 3 substituents selected from the group consisting of halogen and lower alkoxy; $R_2'$ is lower alkyl, lower alkanoyl, lower cycloalkanoyl,

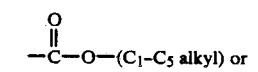

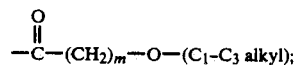

wherein m is 1 to 2.

25. A compound in accordance with claim 24, where $R_2'$ lower alkanoyl.

26. A compound in accordance with claim 25, cis-rac.-6-(acetyloxy)-6,7-dihydro-7-(4-methoxyphenyl)-3-phenyl-1, 4-thiazepin-5(4H)-one.

27. A compound in accordance with claim 25, trans-rac.-6-(acetyloxy)-6,7-dihydro-7-(4-methoxyphenyl)-3-phenyl-1, 4-thiazepin-5(4H)-one.

* * * * *